(12) United States Patent
Gerdil et al.

(10) Patent No.: US 6,890,711 B1
(45) Date of Patent: May 10, 2005

(54) TITRATION METHOD FOR A COMPLEX VIRAL COMPOSITION

(75) Inventors: Catherine Gerdil, Ecully (FR); Jean-Francois Saluzzo, Lyons (FR)

(73) Assignee: Aventis Pasteur, Lyons (FR)

( * ) Notice: Subject to any disclaimer, the term of this patent is extended or adjusted under 35 U.S.C. 154(b) by 0 days.

(21) Appl. No.: 09/402,357

(22) PCT Filed: Apr. 3, 1998

(86) PCT No.: PCT/FR98/00678

§ 371 (c)(1),
(2), (4) Date: Dec. 29, 1999

(87) PCT Pub. No.: WO98/45709

PCT Pub. Date: Oct. 15, 1998

(30) Foreign Application Priority Data

Apr. 4, 1997 (FR) .............................. 97 04371

(51) Int. Cl.[7] .............................. G01N 33/53
(52) U.S. Cl. ............................ 435/5; 435/7.1; 435/7.92
(58) Field of Search ............................ 435/5, 7.1, 7.92

(56) References Cited

FOREIGN PATENT DOCUMENTS

| EP | 0 279 563 | 8/1988 |
|---|---|---|
| FR | 2 511 702 | 2/1983 |
| FR | 2 694 022 | 1/1994 |

OTHER PUBLICATIONS

Ibanez–Bernal et al., Medical and Vertinary Entomology (Oct. 1997) 11(4) 305–9.*

Shaw et al., Gastroenterology, (Nov. 1987) 93(5) 941–50.*

Osterhaus et al., Developments in Biological Standardization (1981) 50, 221–8.*

Medline Abstract, Gastroenterology, (Nov. 1987) 93(5) 941–50, Shaw et al.*

Ibanez–Bernal et al. Medline Abstract Medical and Veterinary Entomology (Oct. 1997) 11(4) 305–9.*

Osterhaus et al., Medline Abstract, Developments in Biological Standardization (1981) 50 221–8.*

Brian WJ Mahy, "A Dictionary of Virology, Second Edition", 1997, pp. 174, 244, Academic Press, New York, New York, USA.

Bernard N. Fields, M.D. et al. (Editors), "Fields Virology", Third Edition, 1996, p. 114, Lippincott–Raven Publishers, Philadelphia, PA, USA.

Patent Abstracts of Japan, vol. 018, No. 596 (P–1825), Nov. 14, 1994 & JP 06 222062 A (Teijin LTD), Aug. 12, 1994, see abstract.

* cited by examiner

Primary Examiner—Laurie Scheiner
(74) Attorney, Agent, or Firm—Burns, Doane, Swecker & Mathis, L.L.P.

(57) ABSTRACT

The invention concerns a method for determining, in a composition containing different species of types of live viruses, the amount of viruses of each type or species, consisting in the following steps: propagating viruses of each type or species on cells permissive to the viruses but not inducing viral interference, assaying each type or species of virus using a specific monoclonal antibody.

5 Claims, No Drawings

TITRATION METHOD FOR A COMPLEX VIRAL COMPOSITION

The invention relates to the field of viral compositions; more specifically the invention relates to a method for determining the virus quantity of each of the species or, more specifically, of each of the serotypes of a given virus species in a composition which contains different species or types of live virus.

Methods for assaying the quantity of each virus species or of each virus type in a viral composition are known in the prior art. The methods which are usually employed consist in using polyclonal antibodies to neutralize the viruses which it is not wished to assay and then in determining the quantity of the remaining virus. This is, in particular, what takes place when there is a need to determine the quantity of attenuated live virus which is present, in the case of each of the I, II and III types, in a composition for vaccinating against polio. However, it is not always possible to implement such methods because it is at times difficult, if not impossible, to neutralize some of the viruses which are present in the composition without interfering with the virus which it is desired to assay, in particular when it is a matter of titrating a vaccine composition which comprises several serotypes of a particular virus, such as the dengue virus, for example. This is because there are no type-specific polyclonal antibodies; monoclonal antibodies which are able to recognize a given type specifically are often not sufficiently neutralizing; sometimes, even, there is no known neutralizing monoclonal antibody. However, in some cases, in particular in the vaccine industry, it is necessary to produce viral compositions which comprise different virus species, or different serotypes of a virus species, in a perfectly defined proportion. Furthermore, pharmaceutical requirements make it necessary to be subsequently able to quantitatively control the composition of the fabricated products in a reliable manner.

It is therefore desirable to be able to have available methods which enable a complex viral composition to be titrated without being modified.

To this end, the present invention relates to a method for determining the virus quantity of each of the virus types or virus species in a composition containing different species or types of live virus, characterized in that it comprises the following steps:

propagating the viruses of each type or species on cells which are permissive for the viruses but which do not induce any viral interference, assaying each type or species of the virus using a specific monoclonal antibody.

The method according to the invention is applied to a composition which comprises several different species of virus and/or several serotypes within one and the same species. The viruses can, in particular, be viruses which are responsible for poliomyelitis, rubella, mumps, measles or dengue, or else rotaviruses. The compositions which comprise these viruses can be vaccine compositions in which the viruses, although having an attenuated virulence, are maintained in the live state. The composition can therefore be, for example, a vaccine composition which comprises the three serotypes of the polio virus or a composition which comprises the four serotypes of the dengue virus. The method according to the invention is of particular interest when the viruses are very closely related antigenically and neutralization of one serotype results, by cross-reaction, in the neutralization of the other serotypes.

According to the invention, the viruses which are present in the composition to be tested are propagated, at various dilutions, on cells which are permissive for the viruses but which do not induce any viral interference. It was thus possible to use Vero cells.

The cells are placed in the wells of plates which are suitable for culturing cells and then inoculated with viral suspensions.

The culture medium used for the viral propagation is a conventional medium which is adjusted in accordance with the nature of the cells which are employed and of the virus to be titrated. After incubating for a time which varies depending on the virus (for example a week in the case of the dengue virus), and at the temperature which is optimal for growing the virus under a $CO_2$ atmosphere, the cell culture supernatants are removed; the cells are then fixed, for example using chilled acetone.

The quantity of viruses present is then determined, for each of the dilutions, using a monoclonal antibody which is specific for the species or the serotype in accordance with the titration performed. The reaction is visualized using a fluorescein-labelled anti-species antibody or using a substrate which is suitable for the ELISA test. The viral titer is determined by the Spearman and Karber method and is expressed as the dose which infects 50% of the cell cultures ($CCID_{50}$).

The same procedure is carried out, in parallel, with each monoclonal antibody which is specific for the species or the type of virus which it is desired to titrate in the viral composition.

It is thus surprisingly possible, using this method, to titrate each serotype which is present in the viral composition without one of the serotypes predominating over the others.

EXAMPLE

Titration of four monovalent vaccine compositions, each of which comprises a serotype of the dengue virus, and of a composition which has been prepared at the time of assay by mixing equal quantities of the four monovalent compositions tested.

The titration is carried out on 96-well microplates in the following manner:

consecutive dilutions of each of the compositions are prepared using MEM culture medium which contains 5% foetal calf serum and 2 g/l of sodium bicarbonate, the viral suspensions which have thus been obtained are inoculated into Vero cells (ref. ATCC:CCL81VERO), which are in layers which have been established for 1 day, at the rate of 10 wells per dilution. Each valency of the monovalent suspensions and of the tetravalent composition is titrated on at least one 96-well plate, the plates are then incubated at 36° C. for one week under 5% $CO_2$, the cell culture supernatants are removed and the cells are fixed on the plates using acetone which has been cooled down to −20° C., the presence of viruses is detected using a monoclonal antibody which is specific for the serotype which is present in the vaccine composition. The antibodies employed are derived from hybridomas supplied by the CDC (Center of Disease Control, Atlanta, USA).

The international 1 serotype is labelled with the antibody derived from the hybridoma D2-1F1-3

The international 2 serotype is labelled with the antibody derived from the hybridoma 3H5-1-12

The international 3 serotype is labelled with the antibody derived from the hybridoma 5D4-11-24

The international 4 serotype is labelled with the antibody derived from the hybridoma 1H10-6-7 the reaction is visualized using a fluorescein-labelled anti-mouse IgG antibody.

The results are read using a fluorescence microscope. The number of wells exhibiting at least one focus of infected (fluorescent) cells is counted in the case of each dilution.

The titer of the product corresponds to the dilution which results in 50% of the cell sheets (that is 50% of the wells) being affected and is calculated by the Spearman and Karber method. It is expressed as the $\log_{10}$ of the $CCID_{50}$.

With each of the assays having been carried out in duplicate, the following results table is obtained:

| | Type 1 | Type 2 | Type 3 | Type 4 |
|---|---|---|---|---|
| Monovalent compositions: | | | | |
| Assay 1 | 3.6 | 4.7 | 5.1 | 2.6 |
| Assay 2 | 3.8 | 4.8 | 5.7 | 2.9 |
| Tetravalent mixture: | | | | |
| Assay 1 | 3.0 | 4.3 | 5.6 | 1.9 |
| Assay 2 | 3.3 | 4.6 | 5.2 | 2.4 |

It is noted that the results which were obtained are in accordance with the expected results; the difference in titer which is observed for each type of virus in the tetravalent mixture varies by about 0.5 $\log_{10}$ $CCID_{50}$, which corresponds to the ¼ dilution to which each serotype is subjected when the mixture is prepared.

Thus, it is possible, in accordance with the invention, to use non-neutralizing monoclonal antibodies to assay each of the serotypes which is present in a viral composition, without inducing any interference between the different serotypes.

What is claimed is:

1. A method for determining virus quantity of each of a virus type or a virus species in a composition which contains different species or types of live virus, comprising the following steps:

(a) propagating the viruses of each type or species on cells which are permissive for the viruses and which do not induce any viral interference, and (b) determining the quantity of each type or species of virus of the composition using a specific monoclonal antibody wherein the quantity of each type of species of virus of the composition bound by the specific antibody is determined;

wherein each monoclonal antibody is virus type or virus species specific;

and wherein the composition comprising different species or types of live virus is a composition which comprises four species or types of live attenuated dengue virus.

2. The method according to claim 1, wherein the propagation is effected on Vero cells.

3. The method according to claim 1, wherein the composition comprising different species or types of live virus is a vaccine composition.

4. The method of claim 1, wherein the propagation of step (a) is performed in serial dilutions of the composition.

5. A method for determining the virus quantity of each of a virus type or virus species in a composition which contains different virus species or virus types of live virus, where each virus species or virus types present in the composition is titrated without impacting quantity of the other virus species or types present in the composition, comprising the steps of (a) propagating the viruses of the composition by adding the viruses to cell cultures in serial dilutions of the composition and culturing the cells;

(b) determining for each dilution the amount of virus type or virus species present using a virus species or virus type specific monoclonal antibody; and (c) performing steps (a) and (b) in the parallel with monoclonal antibodies for each virus species or type;

wherein each type or species present in the composition is titrated without impacting quantity of the other virus species or types present in the composition;

and wherein the composition comprising different species or types of live virus is a composition which comprises four species or types of live attenuated dengue virus.

* * * * *